United States Patent [19]

Podvin

[11] Patent Number: 4,636,078
[45] Date of Patent: Jan. 13, 1987

[54] MICROSCOPIC DETECTION OF MEMBRANE SURFACE DEFECTS THROUGH INTERFERENCE PATTERNS

[75] Inventor: T. Charles Podvin, Poway, Calif.

[73] Assignee: Micromanipulator Microscope Co., Inc., Escondidto, Calif.

[21] Appl. No.: 539,051

[22] Filed: Oct. 4, 1983

[51] Int. Cl.[4] ............................ G01B 9/04; G01B 9/02
[52] U.S. Cl. .................................. 356/359; 350/509; 356/237
[58] Field of Search ............... 356/359, 357, 360, 237, 356/239, 351, 429–431, 345; 350/509, 510, 507, 516–526

[56] References Cited

U.S. PATENT DOCUMENTS

| | | | |
|---|---|---|---|
| 2,687,670 | 8/1954 | Locquin | 350/509 |
| 3,804,532 | 4/1974 | Patten et al. | 356/357 |
| 3,998,553 | 12/1976 | Hunter et al. | 356/359 |
| 4,255,014 | 3/1981 | Ellis | 350/510 |

OTHER PUBLICATIONS

Jenkins et al., "Fundamentals of Optics", McGraw Hill, 1957, p. 235.

Primary Examiner—Vincent P. McGraw
Assistant Examiner—Robert D. V. Thompson, III
Attorney, Agent, or Firm—Fitch, Even, Tabin & Flannery

[57] ABSTRACT

Transparent membranes are examined with a microscope having coaxial brightfield illumination fitted with a narrow bandwidth filter to convert polychromatic light from a source to substantially monochromatic light. Light reflecting off of the surfaces of the membrane recombine to create an interference pattern, including observable fringes in the region of membrane surface aberrations. Membranes which may be examined include pellicles used to cover photomasks and photo-resist layers. If a photo-resist layer is examined, a filter is selected to provide essentially monochromatic light at a wavelength to which the resist is insensitive.

22 Claims, 6 Drawing Figures

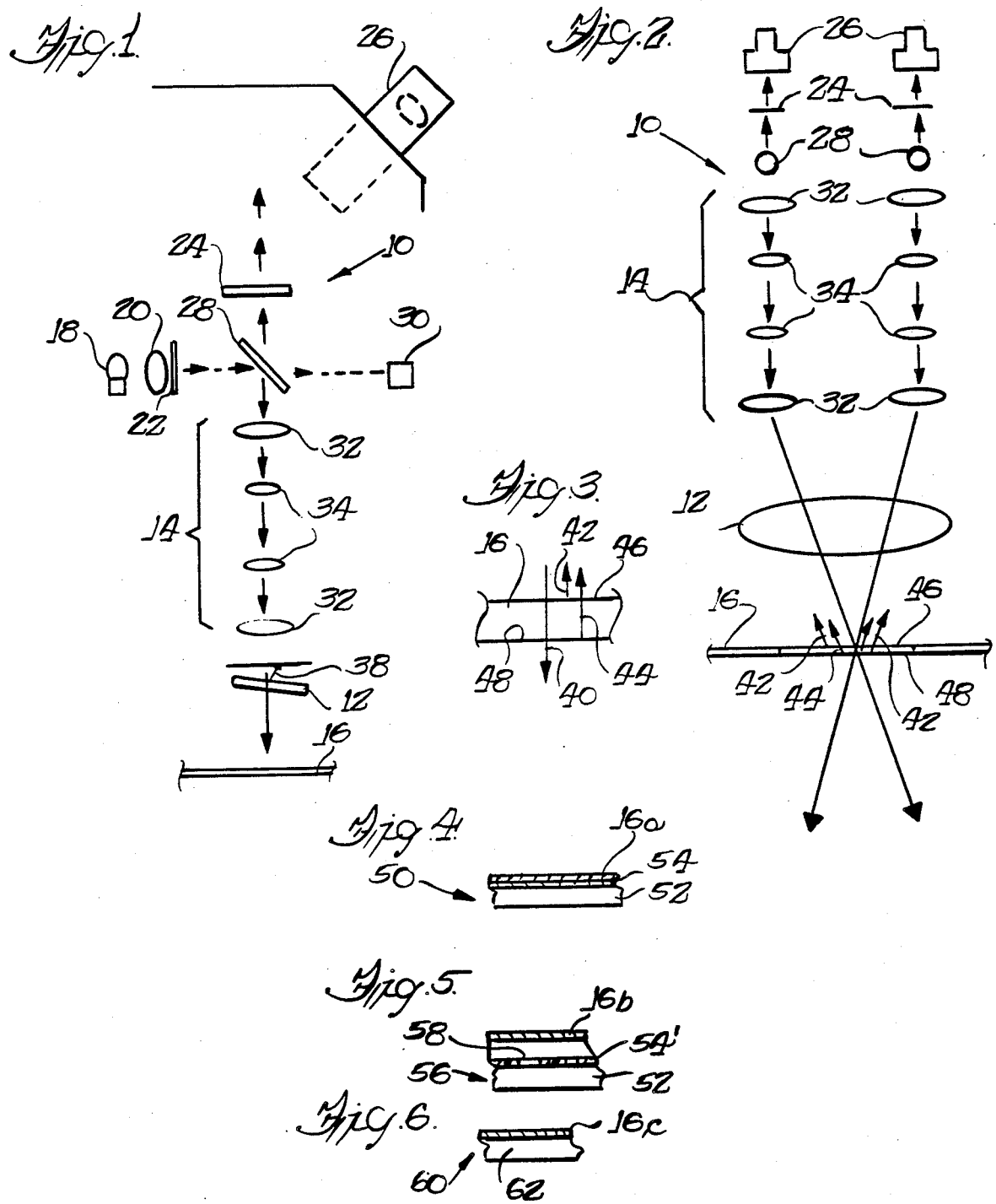

MICROSCOPIC DETECTION OF MEMBRANE SURFACE DEFECTS THROUGH INTERFERENCE PATTERNS

The present invention relates to microscopic inspection of thin transparent membranes and more particularly to detection of defects or aberrations in the membrane by the appearance of interference fringes.

BACKGROUND OF THE INVENTION

The present invention solves problems in inspecting transparent membranes at various stages in the manufacture of integrated circuits on silicon wafers by a microlithography process. However, the invention is applicable to inspection of other thin transparent membranes.

The microlithography technique is similar to photography except that glass coated with etched chrome, called a photomask, serves as the negative from which the integrated circuit is printed. The negative or photomask is formed from a photomask blank comprising a glass plate covered on one surface with a layer of chromium, which is in turn covered with a photo-resist membrane. The resist of the blank is exposed to a focused geometric light pattern, creating a photochemical change in the exposed area. The exposed blank is then subjected to a developing solution that removes exposed resist, and the blank is then exposed to an acid solution which removes the underlying chromium in the regions where the resist has been removed, etching the geometric pattern into the chromium. To protect the developed photomask from dust, the photomask is often packaged as a unit with a membrane or "pellicle" of transparent material, such as nitrocellulose or a PEHB membrane, overlying the etched surface and spaced therefrom by about 3-6 mm.

The pellicle-covered photomask is then used for projecting the geometric pattern onto a silicon wafer that is coated with a thin layer or membrane of photo-resist. By a multi-step process, the exposure pattern is developed into an integrated circuit of the precise projected geometric pattern.

The membrane that is used as the pellicle, the resist layer of the photomask blank and the resist layer covering the silicon wafer are all very thin, the pellicle typically being between about 0.8 and about 3 $\mu$m. thick and the resist layers typically being between about 0.5 $\mu$m. and about 2 $\mu$m. thick. The microlithographic process requires high precision as even the smallest defects can result in an unsuitable product. Defects in either the resist or the pellicle may take the form of very tiny holes, wrinkles, uneven thicknesses and inclusion of particles, including transparent inclusion particles.

Because of the thinness of the resist and pellicle membranes, defects are often very difficult to detect. Defects in pellicles are even difficult to detect under a microscope because the defects do not produce any significant intensity or color change. Presently, in addition to microscopic examination, pellicles are inspected under monochromatic light with an unaided eye. However, this technique does not enable the observer to see low contrast defects having the size of a few hundredths of a millimeter. Furthermore, this is an additional step requiring additional technician time and an additional piece of equipment which occupies bench space.

It would be desirable to have a one-step process for inspecting thin membranes, such as pellicles for photomasks and resist layers.

SUMMARY OF THE INVENTION

The invention provides for microscopic inspection of a substantially transparent membrane by observing the membrane with light that has been filtered through a very narrow bandwidth filter, producing noticeable interference patterns in the regions of imperfections on the membranes. The narrow bandwidth filter acts to convert the light from a polychromatic source, such as a tungsten lamp, to substantially monochromatic light. The membrane itself has two surfaces, each with a certain degree of reflectivity at the monochromatic wave length. Reflections off of the two surfaces split the beam of monochromatic light, and the split beam recombines, creating interference of superimposed light reflected from the two surfaces, and in the regions of membrane irregularities, interference fringes are visible. For inspecting photo-resist layers, a monochromatic wave length is selected which does not expose the resist.

BRIEF DESCRIPTION OF THE DRAWINGS

FIG. 1 is a diagrammatic side illustration of the optics of a stereomicroscope and a narrow band filter used in conjunction with the microscope for examining a thin, transparent membrane;

FIG. 2 is a diagrammatic front illustration of the microscope optics, filter and membrane of FIG. 1;

FIG. 3 is an enlarged diagrammatic illustration showing incident light reflecting off of the membrane surfaces;

FIG. 4 is an enlarged cross-sectional view of a photomask blank;

FIG. 5 is an enlarged cross-sectional view of a pellicle-covered photomask; and

FIG. 6 is an enlarged cross-sectional view of a silicon wafer covered with a resist layer.

DETAILED DESCRIPTION OF THE PREFERRED EMBODIMENT

In accordance with the present invention, a filter having a very narrow bandwidth is placed in the light path of a microscope to convert light from a polychromatic light source to substantially monochromatic light. With the monochromatic light directed through the microscope, the thin transparent membrane functions as an interferometer, reflections of incident light off of the two surfaces of the membrane recombining to create an interference pattern of the doubly reflected light, including detectable interference fringes in the regions of defects or aberrations in the membrane.

The invention takes advantage of the well known phenomenon that a material having two partially reflecting surfaces will reflect light from each of these surfaces, and the light reflected from these surfaces will recombine as superimposed light waves having an amplitude which is the sum of the two superimposed waves. The amplitude of the superimposed waves is maximized by recombination of waves perfectly in phase and cancelled if 180° out of the phase. If two surfaces are perfectly parallel, the intensity of the superimposed reflected waves will be uniform across the membrane; however, if there are irregularities in either of the surfaces, bands or fringes in the vicinity of the irregularities will be darker or lighter.

The interference pattern, including interference fringes, varies for each wave length, and if the light source is polychromatic, the multiple fringe patterns tend to obliterate each other. Thus interference patterns are usually only seen under substantially monochromatic light, and herein it is preferred that the incident light used to observe the membranes should have a half-bandwidth of about 20 nanometers or less and preferably about 10 nanometers or less.

Although it is conceivable that the light source itself could be monochromatic, e.g., a sodium vapor light, a monochromatic source would preclude the use of the microscope for white light observations. It would also be bulkier, generally more expensive, and difficult to retrofit. The purpose of this invention is to add capability by means of a simple retrofit without removing or interfering with the normal microscope functions. Therefore, the invention contemplates the use of the tungsten light bulbs conventionally used with a microscope, in conjunction with a narrow bandwidth filter. The filter should have a half-bandwidth of 20 nanometers or less, and preferably than 10 nanometers or less.

The filter should transmit a good percentage of the incident light at a peak wavelength; however, it is difficult to obtain high transmittance of light in a narrow bandwidth filter. A filter that transmits 25 percent of the incident light at the peak wavelength is generally acceptable, but it is preferred that the filter transmit at least about 50 percent of the incident light at the peak wavelength. A typical filter usable in accordance with the invention is a number AL-5893 filter sold by Corion which has a 50 percent transmittance at 589 nanometers and a half-bandwidth of 10 nanometers.

In order to produce noticeable interference from a pair of reflected surfaces, it is necessary that the two superimposed waves originate from the source at substantially the identical time. This requires that the two reflecting surfaces be very close together, and irregularities in flat membranes having thicknesses between about 0.5 and about 25 microns and preferably between about 1 and about 5 microns are detectable using the methods of the invention.

The membrane material that may be examined must be substantially transparent; however, as is true of all material, some light will be absorbed and some light will be reflected at its surfaces. The surface reflections are, of course, required to superimpose light waves and create the interference patterns. Herein, it is preferred that the membrane transmit at least about 50 percent of the incident light and preferably, the membrane transmits about 90 percent of the incident light. To produce an observable interference pattern, the amount of light reflected at each surface should be between about 0.5 and about 10 percent of the incident light. Although pellicle manufacturers wish to minimize reflection losses; there is still sufficient reflectance to observe significant defects.

Oftentimes, pellicles are coated to reduce reflections, reducing distortions of the projected image. This, of course, tends to weaken the interference pattern. However, as the surface is coated with a material which is intended to reduce reflections at the projected wavelengths, it is frequently possible to find a wavelength where the coating is less effective and good interference patterns in the regions of irregularities appear. Thus a pellicle covering a photomask through which blue light is to be projected, may have a coating which reduces surface reflections of blue light but which may show readily observable interference fringes at longer wavelengths. Otherwise, the wavelength of the monochromatic light is not generally considered to be particularly critical for examining the pellicle; however, for the sake of simplicity, it is desirable that the same filter be used for examining the pellicle as for the resist layers.

A requirement for a light used to inspect a thin layer of photo-resist is that it does not prematurely expose the resist. Resists are available which are exposed by light in a relatively narrow frequency range. In microlithography in the semi-conductor field, it is most common to have a resist which is sensitive to blue light but which is essentially insensitive to yellow light or light further toward the red end of the spectrum. For blue light sensitive resist, therefore, it is desirable to have monochromatic light having a wavelength of about 500 nanometers or longer, allowing careful examination of the resist without risk of premature resist exposure.

The microscope used to examine the membranes may be a compound microscope or a stereomicroscope. Within the magnification ranges which pellicle membranes or resist layers are examined, a stereomicroscope provides a broader field of view and less eyestrain to the technician. To obtain an observable interference pattern, it is necessary that the microscope provide a light path from the light source, through the objective of the microscope, to the subject membrane, back through the objective and to the eyepiece. Such a light path is known by several names, commonly as incident coaxial illumination.

The particular placement of the filter in the light path of the microscope is not considered important so long as the light follows a single path from the source, through the filter, to the membrane and to the eyepiece. The selected position of the filter within the light path depends primarily on the configuration of the microscope. Although the filter could be placed internally, this would require a redesign of existing microscopes and limit the general utility of the microscope. For long-working distance (LWD) objectives, such as those commonly supplied on stereomicroscopes, it is preferred to place the narrow-band filter between the objective of the microscope and the membrane. For compound microscopes, it is usually not practical to place the filter in front of the objective because this would reduce the critical working distance and introduce significant aberrations. Instead, the filter is preferably located in the tray that is normally provided for such purpose as part of the illuminator. It is also possible to place the filter covering the eyepiece, however, with stereomicroscopes having a pair of eyepieces, this arrangement is less convenient.

In order that interference patterns may be observed, it has been found to be important that the narrow bandwidth filter that is placed in the portion of the pathway between the membrane and the objective be tilted at a slight angle to the plane perpendicular to the light path. Otherwise, reflections from the filter surfaces tend to overwhelm the interference patterns created by the small proportions of light reflected by the membrane surfaces. Generally it is found that the filter must be tilted at least about $2\frac{1}{2}°$ to the plane perpendicular to the axial light path. Generally the tilt will be no more than about 5°; otherwise the central wavelength of the filter will shift and image aberrations will increase.

Resist and pellicle membranes are best examined for defects at magnifications of between about 10 and about 100 and preferably between about 10 and about 50.

Examination of a resist layer or a pellicle is facilitated with long working distance (LWD) objectives, which provide clearance for the safe handling of wafers, masks and pellicles. LWD objectives, when used with a polychromatic light source, exhibit chromatic aberrations resulting from the fact that different wavelengths of light produce images of slightly different sizes, and the multiplicity of overlaid images causes the edges of the combined image to be fuzzy. Although the use of colored filters is known to reduce chromatic aberration, the substantial elimination of chromatic aberration leading to a sharp monochromatic image along with the interference pattern seen on very thin membrane by using narrow bandwidth filters has not been previously appreciated. Most commonly, filters that are used merely to prevent chromatic aberration have a relatively wide bandwidth because such filters are much less expensive than the narrow bandwidth filters used to practice the method of the present invention.

To better illustrate the invention, shown in FIGS. 1 and 2 are diagrammatic illustrations of the optical elements of a stereomicroscope 10 and a narrow bandwidth filter 12 disposed below the objective 14 of the microscope for the purpose of viewing interference patterns of a thin transparent membrane 16. The light source comprises a polychromatic lamp 18 disposed laterally relative to the axes of the stereo light paths. In each of the two light paths, the light from the lamp 18 first passes through a condenser lens 20 which collimates the light and then through a polarizer 22, which together with a cross-polarizing filter 24 adjacent the eyepiece 26 reduce the number of internal reflections which reach the eyepiece. A beam-splitting element 28 directs a portion of the incident light axially down the light path to the objective 14 while a second portion of the light passes through the beam-splitter 28 and is lost to a light trap 30. A zoom objective 14 is represented by four lenses including top and bottom stationary lenses 32 and a pair of cam-driven movable lenses 34, however, it is to be understood that the invention is applicably to microscopes having other objective means or systems.

The filter 12 is disposed below the objective 14 and above the observed membrane 16. Because the narrow bandwidth filter reflects a significant amount of light from its surfaces, it is held at a slight angle relative to the axial light paths, whereby reflected light, represented by the arrow 38, is deflected away from the objective 14.

The major portion of the light, represented by the arrow 40 (FIG. 3) passes directly through the transparent membrane that is being observed. However, minor portions, represented by arrows 42 and 44, are reflected upwards off of the surfaces 46 and 48 of the membrane, the reflections off of the closely-spaced surfaces recombining to create the interference pattern that permits detection of aberrations in the membrane 16.

The combined reflections pass through the objective 14, and a portion of the combined reflection continues axially through the beam splitter 28, the cross polarizing filter 24 and to the eyepiece 26 through which interference patterns are observed.

Illustrated in FIG. 4 is a photomask blank 50 consisting of a glass plate 52, a chromium layer 54 covering one surface of the glass and a photo-resist layer 16a covering the chromium layer. Illustrated in FIG. 5 is a photomask 56 comprising a glass plate 52 and the chromium layer 54' which has been etched with a pattern represented at 58. The etched photomask 56 is covered with a thin transparent protective membrane or pellicle 16b. Illustrated in FIG. 6 is a printed circuit blank 60 consisting of a silicon wafer 62 covered with a photoresist layer or membrane 16c. Any of the membranes 16a, 16b or 16c may be observed for aberrations by placing the membranes along with their underlying glass, chromium, or silicon layers in the light path of a microscope having a filter that converts polychromatic light to monochromatic light and having incident brightfield illumination optics.

Several advantages of the invention may now be more fully appreciated. For use in manufacturing integrated circuits, an important application is the inspection of unattached pellicles just prior to mounting on photomasks. Because the filter can be easily changed from rest to duty positions, the same microscope can also be used to inspect the photomask. The result is an efficient use of clean room space and capital equipment. The invention also allows both resist layers and pellicles to be examined for defects at the same microscopic station, each in a single examination. Additionally, the narrow bandwidth of the filter improves the microscopic image quality, particularly when used in conjunction with LWD objectives.

A major advantage of the invention is its simplicity. Microscopes that are currently available are generally adapted to act as an interferometer merely by placement of a narrow bandwidth filter in the optical path. The thin membrane, e.g., either the pellicle or the resist layer, serves as the beam-splitting portion of the interferometer. This is in contrast with interferometer objectives which are currently sold as accessories for microscopes where a mirror within the objective provides a reference surface for an examined reflective surface. In the present invention, the membrane that is being examined provides both of the reflecting surfaces, eliminating the need for a reference mirror. The narrow band filter is, of course, much simpler and less expensive to produce than an interferometer objective.

While the invention has been described in terms of a preferred embodiment, modifications obvious to one with ordinary skill in the art may be made without departing from the scope of the invention.

Various features of the invention are set forth in the following claims.

What is claimed is:

1. An apparatus for inspecting a substantially transarent membrane by reflection when said transparent membrane is backed by an opaque surface, said apparatus comprising:

said transparent membrane having a pair of flat surfaces with a thickness between said pair of flat surfaces of between about 0.5 and about 2.5 microns, said transparent membrane transimtting at least about 50% of incident light at a particular wavelength, and each of said pair of flat surfaces reflecting between about 0.5% and about 5% of the incident light;

a polychromatic light source;

a microscope having an eyepiece and an objective means and defining a light path from said light source through the objective means to said transparent membrane, and back from said transparent membrane, through said objective means, and to the eyepiece;

a filter removably disposed in said light path having a peak transmittance at a particular wavelength with a bandwidth of about 40 nanometers or less;
one of said pair of flat surfaces forming a reference surface and the other one of said pair of flat surfaces forming a measurement surface such that light reflecting off said reference surface and reflecting off said measurement surface to said eyepiece combine to create an observable interference pattern permitting inspection of said transparent membrane for defects, said defects appearing as fringe patterns in regions of change in optical path length; and
said microscope being useful for normal observations of said opaque surface with polychromatic light when said filter is removed from the light path.

2. A combination in accordance with claim 1 wherein said filter has a bandwidth of about 20 nanometers or less.

3. A combination in accordance with claim 1 wherein said particular wavelength is about 500 nanometers or longer, and said membrane is a photo-resist having sensitivity to light of shorter wavelength and essential insensitivity to light at the particular wavelength.

4. A combination in accordance with claim 1 wherein said membreane has a thickness of between about 1 and about 5 microns.

5. A combination in accordance with claim 1 wherein said microscope provides magnification in the range of between 10 and about 100.

6. A combination in accordance with claim 1 wherein said microscope provides magnification in the range of between about 10 and about 50.

7. A combination in accordance with claim 1 including a long-working distance objective in said microscope providing a high magnification, said narrow bandwidth filter eliminating chromatic aberrations.

8. A combination in accordance with claim 7, said filter being disposed between said objective and the membrane.

9. A combination in accordance with claim 1, said filter being disposed between said light source and said microscope.

10. A combination in accordance with claim 1, wherein said membrane is a photo-resist layer.

11. A combination in accordance with claim 1, wherein said membrane is selected from the group consisting of a nitrocellulose membrane and a PEHB membrane.

12. A combination in accordance with claim 1 wherein said filter is disposed in the portion of said light path between said membrane and said eyepiece and tilted at an angle relative to the plane perpendicular to said portion of the light path, whereby reflections from the surfaces of said filter are diverted away from said eyepiece.

13. A method of examining a substantially transparent membrane when backed by an opaque surface, said transparent membrane having a pair of substantially parallel surfaces and a thickness of between about 0.5 and about 25 microns, one of said pair of parallel surfaces forming a reference surface and the other of said pair of parallel surfaces forming a measurement surface, the method comprising:
providing a microscope having an eyepiece, an objective means, and a polychromatic light source positioned to shine light along a light path from said source, through said objective means, through the transparent membrane, onto the opaque surface and then back to said objective means and to the eyepiece;
disposing within said light path a filter having a peak transmittance at a particular wavelength with a bandwidth of about 40 nanometers or less;
placing said transparent membrane in front of said objective means, and
examining said transparent membrane through said eyepiece and noting interference patterns created by light reflecting off of said reference surface and said measurement surface toward said objective means, wherein fringe patterns of the interference patterns are indicative of surface aberrations in said transparent membrane.

14. A method according to claim 13, said microscope providing a magnification of between about 10 and about 100.

15. A method according to claim 13 wherein said filter has a bandwidth of about 20 nanometers or less.

16. A method according to claim 13 wherein said filter transmits at least about 25% of the light at said peak wavelength.

17. A method according to claim 13 wherein said membrane transmits at least about 50% of the incident light at said peak wavelength.

18. A method according to claim 13 wherein said peak wavelength is about 500 nanometers or longer, and said membrane is a photo-resist sensitive to blue light and substantially insensitive to light transmitted through said filter.

19. A method according to claim 13 wherein said membrane is between about 0.5 and about 25 microns thick.

20. A method according to claim 13 wherein said surfaces of said membrane each reflect between about 0.5 and about 5 percent of the incident light.

21. A method in accordance to claim 15, disposing said filter in the portion of said light path between said membrane and said eyepiece at an angle relative to the plane perpendicular to said light path portion.

22. A method of examining an object including an opaque surface and a transparent membrane by alternately examining the opaque surface and the transparent membrane for defects, the transparent membrane having a pair of substantially parallel surfaces and a thickness of between about 0.5 and about 25 microns, one of said pair of parallel surfaces forming a reference surface and the other of said pair of parallel surfaces forming a measurement surface, the method comprising:
providing a microscope having an eyepiece, an objective means, and a polychromatic light source positioned to shine light along a light path from polychromatic light source, through said objective means, and to the object, and to receive light back from the object, through said objective, and to said eyepiece;
disposing said object in front of said objective means perpendicular to said light path such that light passes through said transparent membrane before impinging on said opaque surface;
examining said opaque surface by observing through said eyepiece the image produced by the reflection of polychromatic light from said opaque surface;
alternately examining said transparent membrane by disposing within said light path between said polychromatic light source and said transparent membrane a filter having a peak transmittance at a particular wavelength with a bandwidth of about 40 nanometers or less, and by observing said transparent membrane through said eyepiece; and noting interference patterns created by light reflecting toward said objective means off of said reference surface and measurement surface, wherein fringe patterns in said interference patterns are indicative of surface aberrations in said transparent membrane.

* * * * *